United States Patent [19]
Barfurth et al.

[11] Patent Number: 5,021,596
[45] Date of Patent: * Jun. 4, 1991

[54] ZIRCONIUM CHELATES, THEIR PREPARATION, AND THEIR USE IN PRINTING INKS

[75] Inventors: Dieter Barfurth, Troisdorf-Spich; Claus Lindzus, Cologne; Heinz Nestler, Troisdorf-Eschmar, all of Fed. Rep. of Germany

[73] Assignee: Huels Troisdorf Aktiengesellschaft, Troisdorf, Fed. Rep. of Germany

[ * ] Notice: The portion of the term of this patent subsequent to Jun. 5, 2007 has been disclaimed.

[21] Appl. No.: 314,816

[22] Filed: Feb. 23, 1989

[30] Foreign Application Priority Data

Feb. 25, 1988 [DE] Fed. Rep. of Germany ....... 3805879

[51] Int. Cl.$^5$ ............................................... C07F 7/00
[52] U.S. Cl. .......................................... 556/55; 106/20
[58] Field of Search ............................. 556/55; 106/20

[56] References Cited

U.S. PATENT DOCUMENTS

| | | | |
|---|---|---|---|
| 3,682,688 | 8/1972 | Hughes et al. | 106/20 |
| 4,065,544 | 12/1977 | Hamling et al. | 423/69 |
| 4,160,051 | 7/1979 | Benisek | 427/352 |
| 4,623,738 | 11/1986 | Sugerman et al. | 556/55 |
| 4,931,094 | 6/1990 | Barfurth et al. | 556/55 |

OTHER PUBLICATIONS

Roberts & Caserio, *Basic Principles of Organic Chemistry*, 2nd. Ed. 1977, p. 615.

*Primary Examiner*—Gary P. Straub
*Assistant Examiner*—Stuart L. Hendrickson
*Attorney, Agent, or Firm*—Felfe & Lynch

[57] ABSTRACT

Zirconium(IV) chelates with citric acid ester radicals and optionally with alkoxy groups are prepared from tetraalkoxy zirconate and a citric acid ester; they are useful as components of printing inks.

4 Claims, No Drawings

ZIRCONIUM CHELATES, THEIR PREPARATION, AND THEIR USE IN PRINTING INKS

FIELD OF THE INVENTION

This invention relates to novel zirconium(IV) compounds which are distinguished by good solubility in organic solvents, by their reactivity as catalysts and cross-linking agents, and by a certain stability against hydrolysis.

BACKGROUND OF THE INVENTION

Esters of the hypothetic zirconium(IV) acid, also known as tetraalkyl zirconates, have been known for some time and are widely used, for example, as catalysts in esterification reactions or as cross-linking reagents, for instance for polymers carrying functional groups. To reduce the reactivity of such zirconates as tetrapropyl or tetrabutyl zirconate, which is too pronounced for many applications, the alkyl groups can be replaced by groups having a chelating action, which leads, for example, to zirconium acetyl acetonate. Other organic zirconium compounds of technical importance are acylates, such as zirconium propionate.

Such metallic acid esters find application as additives in flexoprinting inks based on nitrocellulose, cellulose ester derivatives or other suitable printing ink binding agents, in order to improve their adhesion to critical substrates, such as polyolefin films, and their stability against solvents and heat; in comparison to the more frequently used titanates, such as titanium acetyl acetonate, the danger of yellowing of white color shades as well as of interaction with antioxidants is greatly reduced in the case of zirconates. Of the available zirconium compounds none, however, is free of problems: the alkyl zirconates cross-link the ink right in the supply vessel, zirconium acetyl acetonate dissolves extremely poorly in the solvents involved, and zirconium propionate can lead to difficulties as regards odors.

OBJECT OF THE INVENTION

The object, therefore, was to find zirconium compounds whose cross-linking action is reduced as it is in the case of zirconium acetyl acetonate, so that cross-linking of the binding agents to which these compounds are added will not occur until during or after the solvent is evaporated from the printed ink, but which have a comparatively good solubility in ink, for example, and the odor of which is slight.

DESCRIPTION OF THE INVENTION

This object has been attained by the discovery of zirconium(IV) chelates optionally containing alkoxy groups, which are characterized in that they contain esters of citric acid as the chelating agents. These zirconium chelates are used in the above-mentioned printing inks as alcoholic solutions, so that these solutions and their use in printing inks have also been discovered for the attainment of the object stated above.

The alkoxy groups of the novel zirconium chelates have preferably 2 to 4 carbon atoms; for special applications they can also have up to and including 8 carbon atoms, which can also be interrupted by oxygen atoms. The citric acid component of the novel chelates is derived from citric acid partial esters, preferably from the citric acid dialkyl esters, whose alkyl groups have preferably 2 to 4 carbon atoms, generally 1 to 8 carbon atoms.

In the novel chelates, one to four of the alkoxy groups of a zirconic acid ester can be replaced by the above-named citric acid ester groups. Accordingly, the ratio of the alkoxy groups bonded to the central zirconium atom to the citric acid ester groups can be between 3:1 and 0:4.

The novel zirconium chelates can be prepared in simple manner by reacting a tetraalkyl zirconate of the formula

$$Zr(OR)_4$$

wherein R is alkyl of 1 to 8 carbon atoms, with 1 to 4 molequivalents of a citric acid dialkl ester whose alkyl groups have 1 to 8 carbon atoms, preferably 2 to 4 carbon atoms and then distilling off the alcohol formed by the reaction. The reaction is advantageously performed by adding the zirconium acid ester to the citric acid ester which has been heated to the reaction temperature. The reaction temperature is in the range between 20° and 100° C., preferably between 60° and 80° C. The reaction generally goes to completion after a reaction time of 2 to 5 hours when it is performed in the preferred temperature range. To produce the pure ester, all the alcohol that is formed by the reaction is distilled out, including any that was used to dilute the zirconium acid ester and entered the reaction vessel with it.

If it is desired to obtain the alcoholic solutions of the novel zirconium chelates, it is not necessary, of course, to distill out all of the alcohol released by the reaction. In that case only as much alcohol is distilled out as is necessary for producing the chelates in ready-to-use form. In some cases, no alcohol needs to be distilled out. The solutions obtained in this manner have a chelate content in excess of 70% by weight.

When used in printing inks, the solutions, which may optionally be further diluted with alcohol or other solvents, exhibit better properties than titanium acetyl acetonate as regards cross-linking and adhesion. They can be admixed with the printing inks in amounts between 1 and 10 percent by weight, preferably between 1 and 4 percent by weight, and the inks containing them have the advantage that, even when they stand for a relatively long time, no gelling occurs. After the ink has been applied to a substrate, adhesion to the substrate, however, is surprisingly better in comparison to titanium acetyl acetonate.

The inherent color of the novel chelates is light yellow to yellow. White printing inks remain virtually unaltered in color by addition of the novel chelates in the stated amounts. Nor does any discoloration occur when these printing inks are applied to substrates containing antioxidants based on phenol.

A considerable advantage is the liquid state of the product. Furthermore, the product is furthermore more easily miscible and distributable and more soluble in printing inks, for example, than solid zirconium acetyl acetonate.

The printing inks for which the zirconium chelate solutions are used in accordance with the present invention are known printing inks based on binding agents such as nitrocellulose (NC inks) or other cellulose ester derivatives, which are cross-linked by metal acid esters. In comparison to other zirconium compounds, the novel zirconium chelates, however, have none of the disadvantages cited above.

The following examples illustrate the present invention and will enable others skilled in the art to understand it more completely. It should be understood, however, that the invention is not limited solely to the particular examples given below.

EXAMPLES

General Instructions for preparing the zirconium chelates in accordance with the invention Diethyl citrate is weighed into a 1,000 ml flask provided with stirrer, thermometer, dropping funnel and reflux condenser. The tetraalkyl zirconate is added to the well-stirred reaction mixture through the dropping funnel. Then stirring is continued for 30 minutes at 60 degrees C. Then the mixture is cooled and packed (Examples 1 to 8) or the alcohol is distilled out through a vacuum still (Examples 9 to 12).

| Examples 1 to 4: Diethylcitrate complex compounds from n-propylzirconate, alcoholic | | | | | | | |
|---|---|---|---|---|---|---|---|
| | Mixture | | | | Data | | |
| Ex. No. | Diethyl citrate | | n-Propylzirconate* | | $ZrO_2$ cont. | Refractive index $n_D^{20}$ | Density g/ml 20° C. | Viscosity mPa·s 20° C. |
| | g | mol | g | mol | | | | |
| 1 | 248 | 1.0 | 455 | 1.0 | 17.5% | 1.450 | 1.11 | 93 |
| 2 | 347.2 | 1.4 | 318.5 | 0.7 | 13.0% | 1.449 | 1.12 | 104 |
| 3 | 446.4 | 1.8 | 273 | 0.6 | 10.3% | 1.452 | 1.15 | 130 |
| 4 | 446.4 | 1.8 | 204.8 | 0.45 | 8.5% | 1.452 | 1.15 | 162 |

* = n-propyl zirconate: 72 wt. % solution in n-propanol.

| Examples 5 to 8: Diethyl citrate complex compounds from n-butylzirconate, alcoholic | | | | | | | |
|---|---|---|---|---|---|---|---|
| | Mixture | | | | Data | | |
| Ex. No. | Diethyl citrate | | n-Butylzirconate** | | $ZrO_2$ cont. | Refractive index $n_D^{20}$ | Density g/ml 20° C. | Viscosity mPa·s 20° C. |
| | g | mol | g | mol | | | | |
| 5 | 248 | 1.0 | 457 | 1.0 | 17.5% | 1.50 | 1.12 | 140 |
| 6 | 347.2 | 1.4 | 319.9 | 0.7 | 13.0% | 1.458 | 1.13 | 135 |
| 7 | 446.4 | 1.8 | 274.2 | 0.6 | 10.3% | 1.457 | 1.15 | 176 |
| 8 | 446.4 | 1.8 | 205.7 | 0.45 | 8.5% | 1.457 | 1.15 | 215 |

** = n-butylzirconate: 84% solution in n-butanol.

| Examples 9 to 12: Diethyl citrate-zirconium complex compounds, alcohol separated | | | |
|---|---|---|---|
| | | Data | |
| Example No. | Starting material from Example No. | Separated alcohol/ % of theory | Index of refraction $n_D^{20}$ | Viscosity mPa·s, 20° C. |
| 9 | 2 | n-propanol/ 95.9 | 1.485 | 44000 |
| 10 | 4 | n-propanol/ 64.1 | 1.474 | 6100 |
| 11 | 6 | n-butanol/ 107.6 | 1.488 | 13800 |
| 12 | 8 | n-butanol/ 80.5 | 1.478 | 25000 |

In the elemental analysis of the products in accordance with the above Examples 1 to 12, the following results were obtained, expressed in percent by weight, which agree with the calculated percentages by weight for the listed formulas:

| | | C | H | $ZrO_2$ |
|---|---|---|---|---|
| Example 2: | Found | 48.0 | 8.0 | 12.7 |
| for $C_{26}H_{44}O_{16}Zr + 4\ C_3H_8O$ | Calc. | 48.3 | 8.0 | 13.0 |
| Example 3: | Found | 48.1 | 7.9 | 10.1 |
| for $C_{33}H_{52}O_{22}Zr + 5\ C_3H_8O$ | Calc. | 48.3 | 7.7 | 10.3 |
| Example 6: | Found | 49.5 | 8.1 | 13.7 |
| for $C_{28}H_{48}O_{16}Zr + 2.62\ C_4H_{10}O$ | Calc. | 49.9 | 8.0 | 13.3 |
| Example 7: | Found | 49.5 | 7.9 | 10.1 |
| for $C_{34}H_{54}O_{22}Zr + 3.62\ C_4H_{10}O$ | Calc. | 49.6 | 7.7 | 10.5 |
| Example 9: | Found | 44.4 | 6.3 | 17.4 |
| for $C_{26}H_{44}O_{16}Zr$ | Calc. | 44.4 | 6.3 | 17.5 |
| Example 11: | Found | 46.5 | 6.7 | 16.3 |
| for $C_{28}H_{48}O_{16}Zr$ | Calc. | 46.0 | 6.6 | 16.8 |

EXAMPLE 13

Description of the adhesion-mediating action of zirconium chelates in accordance with the invention in nitrocellulose printing ink for polypropylene.

4 weight-percent of the zirconium chalate complex compounds in accordance with the invention (see Table) was added to a nitrocellulose printing ink containing 25 weight-percent of nitrocellulose of Standard Type 34 E, dissolved in a mixture of ethanol and ethyl acetate with titanium dioxide as the white pigment, and the mixture was stirred for a few minutes. By means of a film-drawing spiral the printing ink thus modified was drawn onto polypropylene film previously subjected to a corona discharge treatment, and after 15 minutes of air-drying, it was finish-dried in the convection oven for one minute at 60° C. Then, the adhesion of the printing ink to the polypropylene was determined by the pressure-sensitive tape test:

A pressure-sensitive tape (e.g., Tesafilm) was adhered to an area of about 4 cm² and jerked away.

| Table of the results: | |
|---|---|
| Additive | Removal of _% of the ink |
| According to Example 2 | Approx. 2% |
| According to Example 3 | Approx. 4% |
| According to Example 4 | Approx. 4% |
| According to Example 6 | Approx. 2% |
| According to Example 7 | Approx. 3% |
| According to Example 8 | Approx. 4% |
| Titanium acetyl acetonate (for comparison) | Approx. 5% |

The comparison with titanium acetyl acetonate was performed in the same manner and the same amounts.

EXAMPLE 14

Testing the reaction of the zirconium chelate complex compounds in accordance with the invention with antioxidants When solutions of butylhydroxyanisole (BHA) are mixed with titanium acetyl acetonate solutions severe discoloration occurs. Since compounds such as BHA are also contained as antioxidants in films that are to be printed, the reaction of solutions of the products in accordance with the invention with a BHA solution was tested:

The discoloration is substantially reduced, and therefore the danger of yellowing when films are printed with inks containing the products in accordance with the invention must be considered to be clearly lower.

| Table of the results with solutions of 1 wt. % in isopropanol | |
|---|---|
| Additive | Gardner color number |
| Titanium acetyl acetonate | 11 |
| Per Example 2 | 4 |
| Per Example 4 | 3–4 |

EXAMPLE 15

Viscosity of a nitrocellulose ink after addition of the zirconium chelate complex compounds in accordance with the invention:

The testing medium was a white printing ink containing 25 weight-percent of ester-soluble nitrocellulose to which 4 weight-percent of the test substances were added. The viscosity was determined with a rotary viscosimeter; between tests the mixture was stored at 50° C.

| Table of the results | | | | | |
|---|---|---|---|---|---|
| | Viscosity in mPa · s after storage at 50° C. for | | | | |
| Additive | 1 day | 1 week | 2 weeks | 1 month | 2 months |
| Titanium acetyl acetonate | 560 | 480 | 480 | 440 | 850 |
| Per Example 2 | 700 | 630 | 570 | 420 | 830 |
| Per Example 4 | 700 | 640 | 550 | 530 | 400 |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula $$Zr(OR)_{4-x}(dialkyl\ citrate)_x$$

wherein
x is an integer from 1 to 4, inclusive;
R is alkyl of 1 to 8 carbon atoms;
the alkyl moieties of the citrate are identical alkyls of 1 to 8 carbon atoms; and
when x is 1 or 2, the R's are identical.

2. A compound of claim 1, wherein
R is alkyl of 2 to 4 carbon atoms;
x is an integer from 1 to 4, inclusive;
the alkyl moieties of the citrate are identical alkyls of 2 to 4 carbon atoms; and
when x is 1 or 2, the R's are identical.

3. A compound of the formula $$Zr(OR)_{4-x}(diethyl\ citrate)_x$$

wherein
R is alkyl of 2 to 4 carbon atoms;
x is an integer from 1 to 4, inclusive; and
when x is 1 or 2, the R's are identical.

4. A solution consisting essentially of a compound of the formula $$Zr(OR)_{4-x}(dialkyl\ citrate)_x$$

wherein
R is alkyl of 1 to 8 carbon atoms;
x is an integer from 1 to 4, inclusive;
the alkyl moieties of the citrate are identical alkyls of 1 to 8 carbon atoms; and
when x is 1 or 2, the R's are identical;
in an alkanol of the formula

ROH wherein
R is identical to the R in said compound.

* * * * *